United States Patent [19]

Hakkers et al.

[11] Patent Number: 4,800,763

[45] Date of Patent: Jan. 31, 1989

[54] METHOD OF SAMPLING A FLUID STREAM AND APPARATUS SUITABLE THEREFOR

[75] Inventors: Royce R. D. Hakkers; Martin H. Hagen, both of Apeldoorn, Netherlands

[73] Assignee: VEG-Gasinstituut N.V., Apeldoorn, Netherlands

[21] Appl. No.: 147,780

[22] Filed: Jan. 25, 1988

[30] Foreign Application Priority Data

Feb. 3, 1987 [NL] Netherlands .......................... 8700256

[51] Int. Cl.⁴ .............................................. G01N 1/20
[52] U.S. Cl. .................................... 73/863; 73/863.31; 73/863.81
[58] Field of Search ................. 73/863, 863.01, 863.81, 73/863.31, 863.33

[56] References Cited

U.S. PATENT DOCUMENTS

| | | | |
|---|---|---|---|
| 3,972,225 | 8/1976 | Fort et al. ................................ | 73/28 |
| 3,978,732 | 9/1976 | Dillman . | |
| 4,229,971 | 10/1980 | Ririe, Jr. ............................ | 73/863 X |
| 4,476,733 | 10/1984 | Chiosta et al. ..................... | 73/863 X |
| 4,713,772 | 12/1987 | Carlson ........................ | 73/863.31 X |

FOREIGN PATENT DOCUMENTS 2306211 8/1974 Fed. Rep. of Germany .

Primary Examiner—Tom Noland
Attorney, Agent, or Firm—Weingarten, Schurgin, Gagnebin & Hayes

[57] ABSTRACT

A method and apparatus are disclosed for monitoring a fluid stream with reference to one or more criteria. Successively a number of samples is drawn from the fluid stream that is at least one more than the number of analysis criteria. Each sampling step includes analyzing a portion of the fluid stream and preserving another portion. At intervals, on the ground of a selection criterion, one of the samples preserved is removed and a fresh sample is drawn, whereby—again—a portion of the fluid stream is analyzed and another portion preserved. The arrangement is such that, at all times, one sample is preserved that corresponds with an extreme value of each of the criteria of analysis.

6 Claims, 5 Drawing Sheets

METHOD OF SAMPLING A FLUID STREAM AND APPARATUS SUITABLE THEREFOR

FIELD OF THE INVENTION

This invention relates in general to a method of taking samples from a fluid stream and analyzing such samples.

More specifically, the invention relates to a method of sampling a fluid stream with reference to one or more criteria by semi-continuous sampling and analysis.

BACKGROUND OF THE INVENTION

In the field of sampling and analysis, there is extensive prior art. Most descriptions, however, give detailed guidelines for analyzing the samples, with special emphasis on the physical and/or chemical principles of the analysis and the measuring technique, and the manner of sampling and sample treatment comes second.

It is often desirable to monitor the composition of a fluid stream with reference to a number of criteria during a certain period of time. Examples of such fluid streams are liquids, such as product streams in the process industry, but also gas streams, such as natural gas or flue gases. To monitor the composition, a sample is taken from the fluid stream at certain intervals or continuously, which is subsequently analyzed. In the analysis, one or more parameters must not exceed pre-determined maximum values, and often must not fall below certain minimum values either. Also, it is often desirable to record the amount of the maximum and minimum values which occur or to keep samples corresponding to such values.

Such requirements imposed upon the fluid stream may be imposed by the Government, in the form of legal stipulations (such as environmental requirements, for example, emission values) or may be the result of agreements between producer and buyer with regard to the quality of products supplied. Also, the requirements may be quality guidelines applying within a concern. The parameters in question invariably concern intensive magnitudes, such as chemical composition (concentration), viscosity, optical rotation, etc.

In order that the composition may be monitored, it is necessary to take a sample from the fluid stream, which is supplied to an analyzer. These samples should of course be representative of the composition of the entire fluid stream.

Sampling can be effected in two ways: by random testing or (semi)-continuously. This invention relates to a method in which samples are taken semi-continuously. In it, a sample is taken from the fluid stream at certain intervals, which sample is analyzed to determine the desired parameter value.

One disadvantage of such a method is, however, that the taking of the sample and the subsequent analysis require relatively much time. As a consequence, there is the risk that the parameter value in the fluid has meanwhile been changed by the time the analysis is completed. Generally speaking, therefore, the means will fail to give an adequate impression of the entire fluid stream. The solution of these problems has hitherto only been sought in the use of ever faster, and hence ever more expensive, measuring methods. Generally speaking, however, speed goes to the detriment of accuracy, reliability and quality.

Another disadvantage of existing methods turns out when the analysis has revealed a parameter value that is outside the range permitted. In that case there are two possibilities:

(a) the measurement is faulty
(b) the extreme parameter value has indeed been exceeded.

As the sample has been used, it can no longer be determined which of the two possibilities presented itself. It is desirable, therefore, that an additional sample is available, which is equal to the sample analyzed.

Sometimes it is desirable for other reasons that a sample of the fluid stream is kept when (one of) the analysis-parameters assume(s) an extreme value. By means of such samples it can thus be shown that the composition of the fluid stream has been within the legally or contractually required, or desired limits within a given period of time.

SUMMARY OF THE INVENTION

The present invention provides a method which does not exhibit the disadvantages outlined above. The invention is characterized by drawing successively from the fluid stream a number of samples that is at least one more than the number of analysis criteria, each sampling step including analyzing a portion of the fluid stream and preserving another portion, and then, at intervals, on the ground of a selection criterion, removing one of the samples preserved and drawing a fresh sample, thereby again analyzing a portion of the fluid stream and preserving another portion, the arrangement being such that, at all times, one sample is preserved that corresponds with an extreme value of each of the analysis criteria.

Thus, for example, according to the invention, the mimimum and maximum values of one component of a fluid stream can be monitored at the same time by successively drawing three samples, analyzing for each sample a portion of the fluid stream and preserving another portion, each time removing the sample which as regards composition is intermediate the two other samples and drawing a fresh sample including analyzing a portion of the fluid stream and preserving another portion.

The composition and quality of the fluid stream can also be monitored, however, with reference to a plurality of criteria, in which the number of samples to be drawn and to be preserved is always one more than the number of analysis criteria. Such monitoring can be effected using any measure known for the purpose.

Advantageously, the course of the method according to the invention is controlled by means of a microprocessor which contains the selection criterion to be applied. Besides the microprocessor can provide for the results of the analysis in a given period being printed and/or recorded on a suitable storage medium. A further advantage is now that the samples can be drawn and analyzed fully automatically, so that the fluid stream composition can also be monitored at moments when there are no attendants, for example, at night. Furthermore, at all times samples are present which correspond to an extreme value of an analysis criterion, so that these may again be analyzed by third parties, should this be desired.

The invention further relates to apparatus suitable for carrying out the method as described above. An apparatus of that kind is characterized in that it comprises means for drawing a sample, means for separately storing a number of samples at least one larger than the number of criteria, means for analyzing a sample with regard to the criteria imposed, and means for comparing the last-obtained analysis result with earlier results.

BRIEF DESCRIPTION OF THE DRAWINGS

The present invention will be more fully understood by referring to the following detailed description in conjunction with the accompanying drawings, of which.

DETAILED DESCRIPTION OF THE INVENTION

Figure 1:
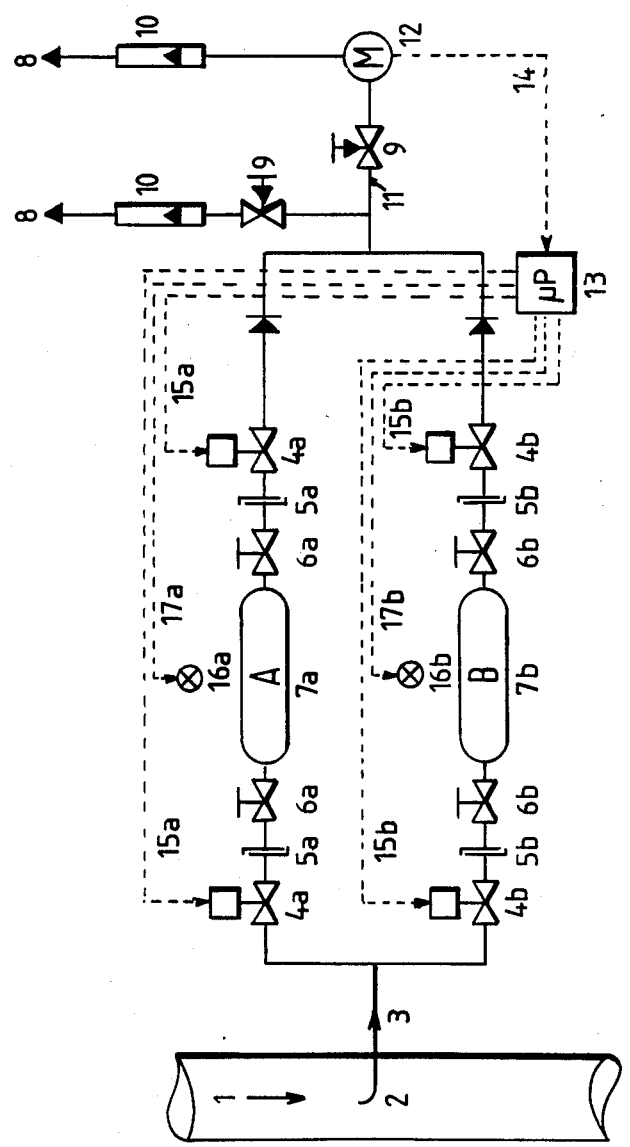
FIG. 1 is a schematic representation of an apparatus constructed and used in accordance with the instant invention.

The apparatus will now be described in more detail with reference to the accompanying diagrammatic drawings. In FIG. 1 of the drawings, 1 designates a pipeline containing a fluid stream whose composition should be monitored. 2 designates the sampling inlet, and 3 the sampling conduit. The sample then arrives via the magnetic valves 4a (or 4b), which are externally operable, and connectors 5a (or 5b) in the sampling cylinders 7a (or 7b). 6a and 6b are manually operable valves. The figure further shows blow-off piping 8, needle valves 9, rotameters 10 (flow indicators), measuring ducts 11, a measuring instrument 12, a microprocessor 13 with signal lines 14 to the measuring instrument, signal lines 15a, b to the magnetic valves, and signal lines 17a and b to indicator lamps 16a and b and non-return valves 18.

The operation of the apparatus is as follows.

In the initial situation, cylinders 7a and 7b are placed in the apparatus, and cylinder valves 6a and 6b are opened. Magnetic valves 4a and 4b are closed.

From the microprocessor, the magnetic valves 4a for cylinder A (7a) are opened. After a sufficient scavenging time, the measuring instrument 12 starts the measurement. During this procedure, generally speaking, the magnetic valves 4a are again closed, although it is clear that they may also be closed after the measurement, depending on the measuring system. After completion of the measurement, the value measured is stored in the microprocessor 13 as associated with cylinder A.

From the microprocessor, the magnetic valves 4a for cylinder B (7b) are opened. After a sufficient scavenging time, the measuring instrument 12 proceeds to measure. During this, or if desired thereafter, the magnetic valves 4b are closed. After completion of the measurement, the value measured is stored in the microprocessor 13 as associated with cylinder B.

As soon as both cylinders contain a sample, it is determined by means of microprocessor 13, and with reference to a selection criterion, which cylinder (A or B) contains the more important sample of the two. At the same time, the microprocessor retains the value measured for this sample. By means of an indicator lamp (16a or b) the sampling apparatus is capable of indicating which cylinder contains the more important sample.

The magnetic valves 4a or 4b of the cylinder containing the less important sample are opened. After a sufficient scavenging time, the measuring apparatus 12 proceeds to measure. During this, or if desired thereafter, the magnetic valves are again closed. After completion of the measurement, the value measured is passed to the microprocessor, where it is again determined which cylinder now contains the more important sample, and which value is to be assigned to the samples in the cylinders. After this evaluation, the sampling apparatus can indicate by means of an indicator lamp which cylinder contains the more important sample. This procedure can be repeated at a desired frequency for a desired period of time (a day, a week etc.).

Sampling is stopped. All magnetic valves 4a and 4b are closed. The valves 6a and 6b on the cylinders are closed. The cylinders are coded and, if desired, the value measured for the sample in the cylinder is indicated by means of a sticker. The cylinders 7a and 7b are uncoupled at connectors 5a and 5b and replaced by fresh cylinders.

Immediately after removal of the full cylinders, fresh cylinders can be connected, whereafter the cylinder valves are again opened, if desired, and sampling can be resumed as indicated.

The uncoupled cylinders, and in particular the cylinder containing the more important sample, can be analyzed in more detail at a suitable laboratory.

Figure 2:
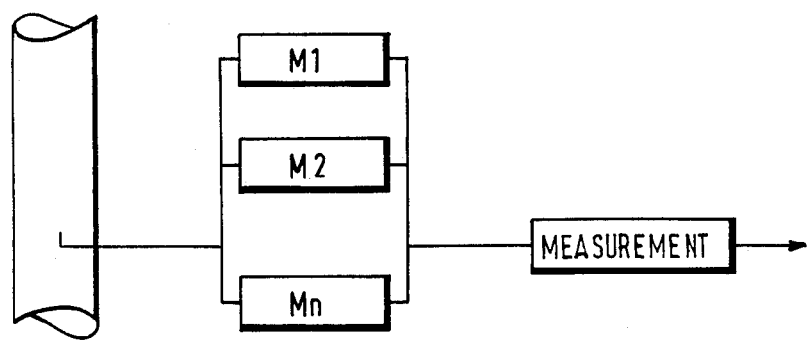
FIG. 2 is diagrammatic representation of how the apparatus of FIG. 1 can be alternatively constructed and used in accordance with the instant invention with more than two cylinders.

FIG. 2 diagrammatically shows that more than two cylinders can be used.

Figure 3:
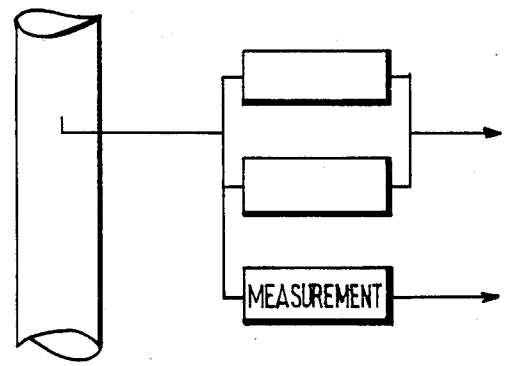
FIG. 3 is a diagrammatic representation of how measurements can be taken in accordance with the instant invention in parallel.
Figure 4:
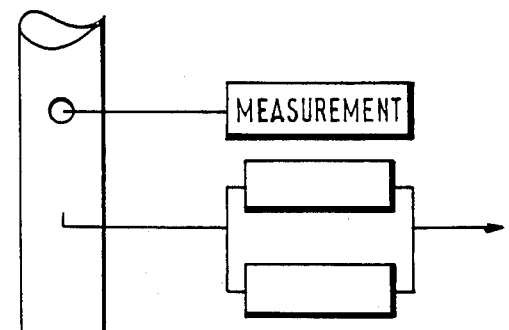
FIG. 4 is a diagrammatic representation of how measurements can be taken in accordance with the instant invention directly in the main stream by means of a sensor.

FIG. 3 diagrammatically indicates how the measurement can be performed in parallel, and FIG. 4 shows that the measurement can be effected direct in the main stream by means of a sensor.

EXAMPLE I

The quality of distribution natural gas is monitored with reference to the Wobbe index. The Wobbe index is a gas quality parameter that is important with regard to the safety of gas consumption, which, according to the area of distribution, may vary within a narrow range.

Figure 5:
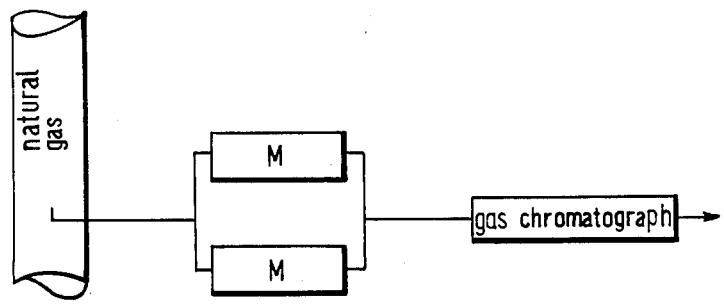
FIG. 5 is a diagrammatic representation of how the instant invention can be used to monitor the quality of distribution natural gas.
Figure 6:
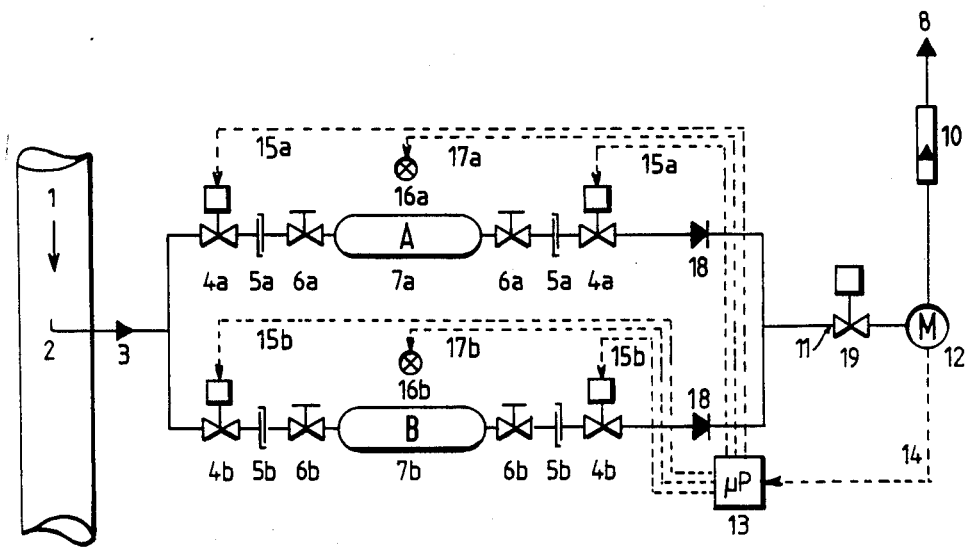
FIG. 6 is a schematic representation of an apparatus constructed and used in accordance with the instant invention to measure the quality of distribution natural gas.

The principle of the assay is shown diagrammatically in FIG. 5. The apparatus used for the assay is constructed as illustrated in FIG. 6, in which the numerals have the same meaning as in FIG. 1. The apparatus is executed in stainless steel as much as possible.

The measuring instrument used is a Hewlett-Packard HP-5890 gas chromatograph, equipped with a 3392 A integrator. The microprocessor is a suitably equipped and programmed Hewlet-Packard HP-86. The remote-controlled valves are magnetic valves. As these can only maintain a presssure differential in one direction, a non-return valve 18 is disposed between the last magnetic valves and the inlet of the gas chromatograph in each duct. In this embodiment, the sample stream through the sampling apparatus and the measuring system is determined by the prevailing prepressure (in this case: an overpressure of 8 bar) and the dimensions of the gas sample valve placed in the gas chromatograph. The cylinders have a volume of 0.5 l. The flow rate through the cylinder and the measuring apparatus is shown by the rotameter. The amount of sample is more than sufficient for a plurality of extremely accurate analyses, if desired by more than one laboratory. The apparatus is used to find the maximum Wobbe index from samples drawn at one-hour intervals through a monthly period.

This process proceeds as follows. Initially all valves are closed. First the cylinder valves 6a and 6b are opened by hand. At time t=0, the microprocessor opens magnetic valves 4a and 19. After a scavenging time of 5 minutes, first valve 19 is closed, whereafter a sample is introduced into the gas chromatograph when flow has stopped ("stop flow"), which can be seen from the zero position on rotameter 10. Thereafter magnetic valve 4a is closed. The results of the analysis are stored in the microprocessor. At time t=60 minutes, valves 4b are opened. 5 minutes later, another sample is introduced into the gas chromatograph, and valves 4b are closed. At time t=120 minutes and each hour thereafter, the microprocessor opens the valves (4a or 4b) associated with the cylinder which, according to the analysis, contains the sample having the lower Wobbe index. The result is that the sample containing the highest Wobbe index measured so far is always preserved. Thus, after one month, a cylinder is available containing natural gas with the highest Wobbe index measured during that month.

EXAMPLE II

Figure 7:
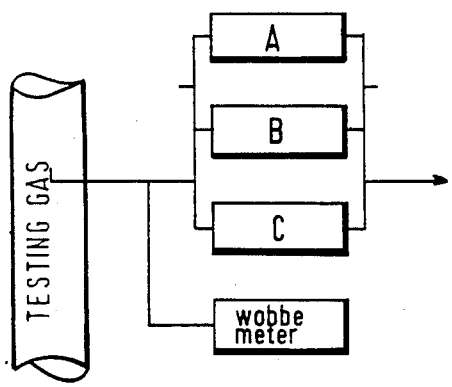
FIG. 7 is a diagrammatic representation of how the instant invention can be used for the quality control of testing gases.
Figure 8:
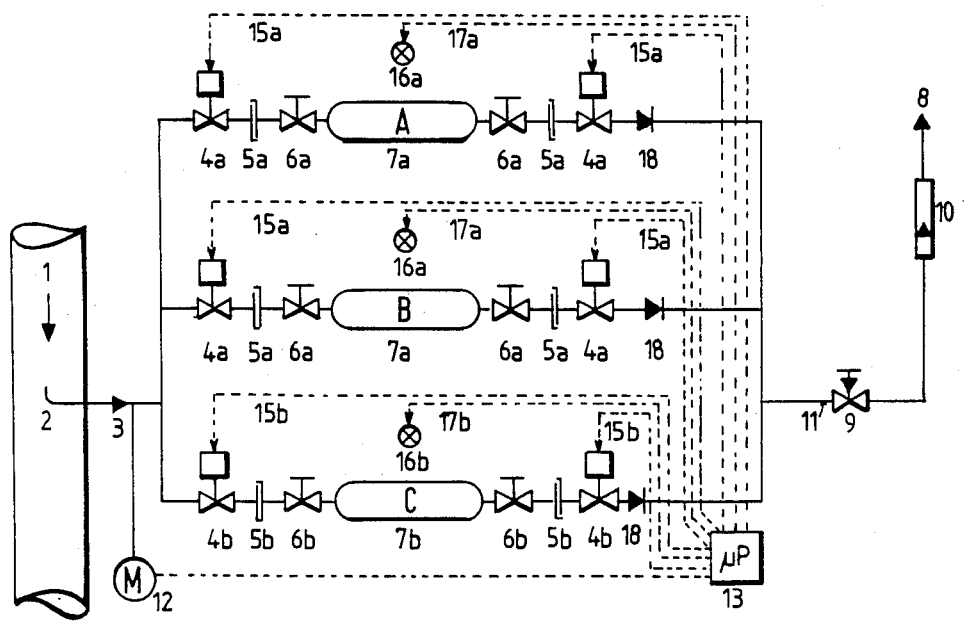
FIG. 8 is a schematic representation of an apparatus constructed and used in accordance with the instant invention for the quality control of testing gases.

An apparatus largely similar to that used in Example I, but comprising three rather than two sampling cylinders, is used for the quality control of testing gases. These testing gases are used to test combustion devices for their specifications. The requirement applying is that a certain maximum value of the Wobbe index must not be exceeded, while the gas may not fall below a certain minimum value. The principle of the assay is shown diagrammatically in FIG. 7, and the apparatus used in FIG. 8. In FIG. 8, the numerals again have the same meaning as in FIG. 1. In each duct non-return valves 18 are disposed.

The operation of the apparatus is similar to Example I. The Wobbe meter (Apparatenbau J.H. Reineke GmbH, Bochum, Western Germany) generates a continuous measuring signal. This is read via a volt meter with a Hewlett-Packard HP-IB interface into a HP-86 microprocessor. The Wobbe meter has a response time of about 1 minute. The flow through the sampling apparatus is controlled with a needle valve 7 to be about 300 l/h.

On the ground of the values read-in, the microprocessor controls the sampling apparatus through an interface. Placed in the sampling apparatus are three cylinders. The HP-86 is programmed so that, at all times, one of the cylinders contains the gas with the lowest Wobbe index measured, one of the cylinders contains the gas with the highest Wobbe index measured, and one cylinder contains the sample which corresponds to the gas measured at that moment. When the Wobbe index of the measured sample is lower than the lowest value so far measured, or higher than the highest value so far measured, the sample is preserved. At each next sampling step, that sample is removed, by opening the magnetic valves concerned, which as regards Wobbe index is intermediate the samples in the two other cylinders.

In this way, after one month, there are samples of the gas stream corresponding to the minimum and maximum values of the Wobbe index as measured in the course of that month.

Example III

Figure 9:
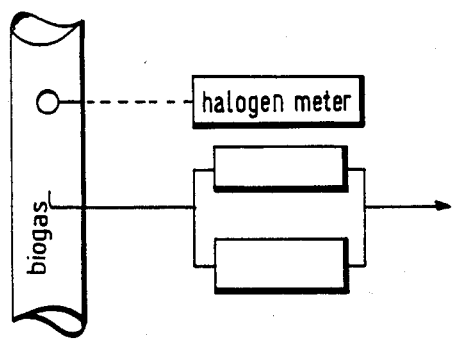
FIG. 9 is a diagrammatic representation of how the instant invention can be used to safeguard gas-fired appliances from excessive halogen concentrations in biogas.
Figure 10:
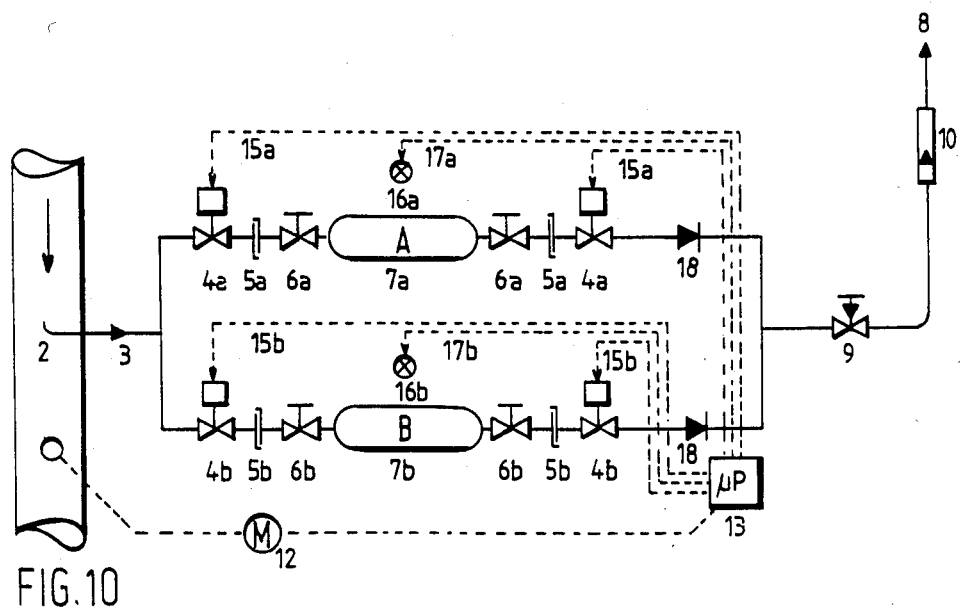
FIG. 10 is a schematic representation of an apparatus constructed and used in accordance with the instant invention to safeguard gas-fired appliances from excessive halogen concentration in biogas.

An apparatus largely similar to that used in Example I is used to safeguard gas-fired appliances from excessive halogen concentrations in biogas. The apparatus is placed next to a biogas pipeline containing biogas under an overpressure of 2 bar. Provided in the pipeline is a halogen sensor, which is connected to the microprocessor. The apparatus used is a Carlo-Erba gas chromatograph, type 4130, with an Electron Capture Detector (Ni 63, 10 mCi). The principle of the measurement is illustrated diagrammatically in FIG. 9. The apparatus is shown in FIG. 10, in which the numerals have the same meaning as in FIG. 1. Moreover, in each duct, non-return valves 18 are disposed Via the accompanying reader and an interface, the values measured are read into a Hewlett-Packard HP-86, which, just as in the preceding examples controls the sampling apparatus. Similarly to Example I, samples are drawn at one-hour intervals, and each time the sample with the lower halogen concentration is removed at the next cycle. The process is in principle continued continuously.

It is only if exceptional values are registered that the sample in question is sent to the laboratory to see, by means of a gas chromatograph with mass-spectometric detection, which components have caused this exceptional signal.

What we claim is:

1. A method of sampling a fluid stream with reference to one or more criteria by drawing samples and analysis, characterized by drawing successively from the fluid stream a number of samples that is at least one more than the number of analysis criteria, each sampling step including analyzing a portion of the fluid stream and preserving another portion, and then, at intervals, on the ground of a selection criterion, removing one of the samples preserved and drawing a fresh sample, thereby again analyzing a portion of the fluid stream and preserving another portion, the arrangement being such that, at all times, one sample is preserved that corresponds with an extreme value of each of the criteria of analysis.

2. A method as claimed in claim 1, characterized by monitoring the minimum and maximum values of one component of a fluid stream by drawing three samples.

3. A method as claimed in claim 1, characterized in that the fluid stream is analyzed by a measurement in the main stream.

4. A method as claimed in claim 1, characterized in that the process is controlled by means of a microprocessor. processor.

5. A method as claimed in claim 1, characterized in that the length of the intervals between the sampling steps is pre-determined.

6. Apparatus suitable for the application of the method as claimed in claim 1, characterized in that the apparatus comprises means for drawing a sample, means for separately storing a number of samples at least one larger than the number of criteria, means for analyzing a sample with regard to the criteria imposed, and means for comparing the last-obtained analysis result with earlier results.

* * * * *